United States Patent
Kravtchenko et al.

(10) Patent No.: US 7,494,513 B2
(45) Date of Patent: Feb. 24, 2009

(54) DIRECT EMULSION FOR BLEACHING HAIR

(75) Inventors: Sylvain Kravtchenko, Shanghai (CN); Claude Dubief, Le Chesnay (FR)

(73) Assignee: L'Oreal, Paris (FR)

( * ) Notice: Subject to any disclaimer, the term of this patent is extended or adjusted under 35 U.S.C. 154(b) by 142 days.

(21) Appl. No.: 11/411,880

(22) Filed: Apr. 27, 2006

(65) Prior Publication Data
US 2006/0242773 A1      Nov. 2, 2006

Related U.S. Application Data

(60) Provisional application No. 60/688,348, filed on Jun. 8, 2005.

(30) Foreign Application Priority Data
Apr. 29, 2005   (FR)   .................................. 05 51120

(51) Int. Cl.
*A61Q 5/10*          (2006.01)
(52) U.S. Cl. ........................ 8/405; 8/406; 8/407; 8/408; 8/410; 8/521; 8/107; 8/111
(58) Field of Classification Search ....................... 8/405, 8/406, 407, 408, 410, 521, 107, 111; 453/432
See application file for complete search history.

(56) References Cited

U.S. PATENT DOCUMENTS

| | | | | |
|---|---|---|---|---|
| 5,196,029 A * | 3/1993 | Kawase et al. | ................. | 8/405 |
| 5,817,155 A * | 10/1998 | Yasuda et al. | ................... | 8/406 |
| 6,290,943 B1 * | 9/2001 | Naser et al. | .............. | 424/70.15 |
| 2004/0141930 A1 * | 7/2004 | Legrand | ...................... | 424/62 |
| 2004/0235700 A1 | 11/2004 | Legrand et al. | | |

FOREIGN PATENT DOCUMENTS

| | | |
|---|---|---|
| EP | 1 291 006 | 3/2003 |
| EP | 1 430 875 | 6/2004 |
| WO | WO 03/011216 | 2/2003 |

* cited by examiner

*Primary Examiner*—Eisa B Elhilo
(74) *Attorney, Agent, or Firm*—Oblon, Spivak, McClelland, Maier & Neustadt, P.C.

(57) ABSTRACT

A direct emulsion for bleaching keratin fibers, preferably human keratin fibers such as hair, having an inert phase containing of a nonoxygenated and nonperfluorinated liquid compound having a water-solubility at 25° C. of less than 1% and an aqueous hydrogen peroxide solution, a bleaching method using this direct emulsion, as it is or in the form of a ready-to-use composition, and the use of this direct emulsion for bleaching keratin fibers. The direct emulsion in accordance with the invention makes it possible to rapidly obtain substantial lightening of keratin fibers while limiting the degradation of the keratin fibers and skin irritation.

22 Claims, No Drawings

DIRECT EMULSION FOR BLEACHING HAIR

REFERENCE TO PRIOR APPLICATIONS

This application claims priority to U.S. provisional application 60/688,348 filed Jun. 8, 2005, and to French patent application 0551120 filed Apr. 29, 2005, both incorporated herein by reference.

FIELD OF THE INVENTION

The subject of the present invention is a direct emulsion useful, for example, for bleaching keratin fibers, and in particular human keratin fibers such as the hair.

Additional advantages and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. The description is to be regarded as illustrative in nature, and not as restrictive.

BACKGROUND OF THE INVENTION

When a person wishes to radically change hair colour, in particular when they wish to obtain a lighter colour than the original colour, it is often necessary to bleach the hair. To do this, bleaching products are used. This bleaching step is optionally combined with a step for dyeing the hair.

It is known to bleach keratin fibers, and in particular human keratin fibers such as the hair, with bleaching compositions containing one or more oxidizing agents. Among the oxidizing agents conventionally used, there may be mentioned hydrogen peroxide, compounds capable of producing hydrogen peroxide by hydrolysis, such as urea peroxide, or persalts such as perborates, percarbonates and persulphates, hydrogen peroxide and persulphates being particularly preferred.

Bleaching compositions are provided mainly in the form of anhydrous products, powders or creams, containing alkaline compounds such as amines or alkali metal silicates, and a peroxygenated reagent such as ammonium or alkali metal persulphates, perborates or percarbonates which are diluted at the time of use with an aqueous hydrogen peroxide composition.

Bleaching compositions may also result from mixing, at the time of use, an anhydrous powder containing the peroxygenated reagent with an aqueous composition containing the alkaline compounds and another aqueous composition containing hydrogen peroxide.

To obtain a product for bleaching keratin fibers which is more effective in terms of lightening and/or speed, it is in theory possible to increase the hydrogen peroxide concentration in the aqueous hydrogen peroxide composition. However, a high hydrogen peroxide concentration can cause degradation of the keratin fibers and possibly skin irritation. Conventionally, in conventional bleaching compositions, the hydrogen peroxide concentration is therefore limited to 12% by weight, or even to 6% by weight.

Moreover, patent application EP 0,193,471 proposes bleaching the hair with an anhydrous hydrogen peroxide solution in an organic solvent.

There has also been proposed, in patent application WO 03/011216, a composition for bleaching the hair which is provided in the form of a direct or inverse emulsion containing an aqueous hydrogen peroxide solution and an organic phase comprising at least one perfluorinated compound.

However, the results obtained in terms of lightening are not yet satisfactory.

OBJECTS OF THE PRESENT INVENTION

One object of the present invention is to provide novel lightening products which are more effective than the lightening products known in the prior art while limiting degradation of keratin fibers and skin irritation.

SUMMARY OF THE INVENTION

The above object is achieved with the present invention whose subject is a direct emulsion for bleaching keratin fibers, comprising an inert phase comprising at least one nonoxygenated and nonperfluorinated liquid compound having a water-solubility at 25° C. of less than 1% and an aqueous hydrogen peroxide solution, the inert phase representing at least 20% by weight of the total weight of the direct emulsion.

The direct emulsion in accordance with the invention makes it possible to rapidly obtain substantial lightening of keratin fibers while limiting the degradation of the keratin fibers and skin irritation.

The subject of the present invention is also a ready-to-use bleaching composition resulting from mixing the direct emulsion in accordance with the invention with one or more compositions each comprising at least one compound chosen from an alkaline agent, a persalt, a direct dye and an oxidation dye precursor.

Another subject of the present invention is a method for bleaching keratin fibers using the direct emulsion or the ready-to-use bleaching composition in accordance with the invention, and a kit for carrying out this method.

Another subject of the invention is the use of the direct emulsion or of the ready-to-use bleaching composition in accordance with the invention for bleaching keratin fibers.

DETAILED DESCRIPTION OF THE PREFERRED EMBODIMENTS

In the context of the invention, a direct emulsion is understood to mean an emulsion containing a continuous aqueous phase.

In the context of the present invention, an inert phase is understood to mean a phase which is chemically inert towards hydrogen peroxide. In the context of the invention, a phase is inert if the degradation of hydrogen peroxide in the presence of this phase is less than 25% after 15 hours at 100° C.

In the context of the present invention, a nonoxygenated and nonperfluorinated liquid compound is understood to mean any nonoxygenated or nonperfluorinated organic or inorganic derivative capable of running and having a viscosity at 25° C. of less than 5000 Poises at a shear rate of 1 $s^{-1}$. This viscosity may be determined with the aid of a RHEOMAT 180 type viscometer.

According to a particular embodiment of the invention, a direct emulsion is provided, comprising an inert phase and an aqueous hydrogen peroxide solution, said inert phase comprising at least one nonoxygenated and nonperfluorinated liquid compound having a water-solubility at 25° C. of less than 1%, the inert phase representing at least 20% by weight of the total weight of the direct emulsion.

According to a particular embodiment of the invention, the inert phase comprises at least one chosen from polyalphaolefins, polybutenes and polyisobutenes, mineral oils, paraffin oils, polystyrene and polyisoprene block copolymers such as liquid Kratons, and mixtures thereof.

According to a particular embodiment, the inert phase represents between 20 and 95% by weight, and preferably between 30 and 90% by weight of the total weight of the direct emulsion.

The direct emulsion in accordance with the invention generally has a hydrogen peroxide concentration of between 1 and 20% by weight, preferably between 2 and 12% by weight of the total weight of the direct emulsion.

According to a particular embodiment, the direct emulsion of the invention comprises at least one compound chosen from anionic, nonionic, cationic and amphoteric surfactants having one or more linear or branched $C_6$-$C_{22}$ alkylated chains and/or one or more perfluorinated chains, amphiphilic polymers such as water-soluble or water-dispersible amphiphilic block copolymers, oxyethylenated or nonoxyethylenated, telechelic or graft associative polymers bearing on their main chain $C_6$-$C_{22}$ alkyl and/or aryl groups, it being possible for these polymers to have a cationic, anionic, amphoteric or nonionic charge, and thickening polymers such as crosslinked acrylic polymers, natural or modified polysaccharides.

These compounds may each be present in the direct emulsion in accordance with the invention in a quantity of, e.g., between 0.1 and 30% by weight, and preferably between 0.2 and 15% by weight of the total weight of the direct emulsion.

The direct emulsion in accordance with the invention preferably has a pH of less than 5. The pH may be adjusted to the desired value by means of acidic or alkaline agents customarily used in cosmetics or with the aid of conventional buffer systems.

Among the acidic agents, there may be mentioned, by way of example, inorganic or organic acids such as hydrochloric acid, orthophosphoric acid, sulphuric acid, carboxylic acids such as acetic acid, tartaric acid, citric acid, lactic acid, and sulphonic acids.

Among the alkaline agents, there may be mentioned, by way of example, ammonium hydroxide, alkali metal carbonates, alkanolamines such as di- and triethanolamines and their derivatives, sodium or potassium hydroxides and the compounds of the following formula (III):

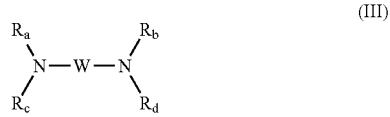

(III)

in which W is a propylene residue optionally substituted with a hydroxyl group or a $C_1$-$C_4$ alkyl radical; $R_a$, $R_b$, $R_c$ and $R_d$, which may be identical or different, represent a hydrogen atom, a $C_1$-$C_4$ alkyl radical or a $C_1$-$C_4$ hydroxyalkyl radical.

To bleach keratin fibers, the direct emulsion in accordance with the invention may be applied as it is to the keratin fibers. It may also be mixed at the time of use with one or more compositions in which at least one alkaline agent and/or at least one persalt and/or at least one direct dye and/or at least one oxidation dye precursor are distributed in order to give a ready-to-use bleaching composition.

In the case where the ready-to-use bleaching composition comprises at least one direct dye and/or at least one oxidation dye precursor, lightening dyeing is carried out, that is to say that bleaching and dyeing of the keratin fibers are simultaneously obtained.

The alkaline agent(s) may be chosen from organic amines, ammonium hydroxide and silicates.

When the ready-to-use bleaching composition in accordance with the invention comprises one or more alkaline agents, they are generally present in a quantity of between 0.01 and 40% by weight, and preferably between 0.1 and 30% by weight of the total weight of the ready-to-use composition.

The persalt(s) may be chosen for example from ammonium or alkali metal perborates, percarbonates and persulphates.

When the ready-to-use bleaching composition in accordance with the invention comprises one or more persalts, they are generally present in a quantity of between 10 and 70% by weight, and preferably between 20 and 60% by weight of the total weight of the ready-to-use composition.

The direct dye(s) may be chosen from the direct dyes conventionally used in direct dyeing. By way of examples, these direct dyes are chosen from nitro dyes of the benzene series, azo direct dyes, methine direct dyes, quinone direct dyes, azine direct dyes, triarylmethane direct dyes, indoamine direct dyes, natural direct dyes. These direct dyes may be of a nonionic, anionic or cationic nature.

Among the benzene direct dyes, there may be mentioned 1,4-diamino-2-nitrobenzene, 1-amino-2-nitro-4-(β-hydroxyethylamino)benzene, 1-amino-2-nitro-4-bis(β-hydroxyethyl)aminobenzene, 1,4-bis(β-hydroxyethyl-amino)-2-nitrobenzene, 1-β-hydroxyethylamino-2-nitro-4-bis(β-hydroxyethylamino)benzene, 1-β-hydroxyethylamino-2-nitro-4-aminobenzene, 1-β-hydroxyethylamino-2-nitro-4-(ethyl)(β-hydroxyethyl)aminobenzene, 1-amino-3-methyl-4-β-hydroxyethylamino-6-nitrobenzene, 1-amino-2-nitro-4-β-hydroxyethylamino-5-chlorobenzene, 1,2-diamino-4-nitrobenzene, 1-amino-2-β-hydroxyethylamino-5-nitrobenzene, 1,2-bis(β-hydroxyethylamino)-4-nitrobenzene, 1-amino-2-[tris(hydroxymethyl)methylamino]-5-nitrobenzene, 1-hydroxy-2-amino-5-nitrobenzene, 1-hydroxy-2-amino-4-nitrobenzene, 1-hydroxy-3-nitro-4-aminobenzene, 1-hydroxy-2-amino-4,6-dinitrobenzene, 1-β-hydroxyethyloxy-2-β-hydroxyethylamino-5-nitrobenzene, 1-methoxy-2-β-hydroxyethylamino-5-nitrobenzene, 1-β-hydroxyethyloxy-3-methylamino-4-nitrobenzene, 1-β,γ-dihydroxypropyloxy-3-methylamino-4-nitrobenzene, 1-β-hydroxyethylamino-4-β,γ-dihydroxypropyloxy-2-nitrobenzene, 1-β,γ-dihydroxypropylamino-4-trifluoromethyl-2-nitrobenzene, 1-β-hydroxyethylamino-4-trifluoro-methyl-2-nitrobenzene, 1-β-hydroxyethylamino-3-methyl-2-nitrobenzene, 1-β-aminoethylamino-5-methoxy-2-nitrobenzene, 1-hydroxy-2-chloro-6-ethylamino-4-nitrobenzene, 1-hydroxy-2-chloro-6-amino-4-nitrobenzene, 1-hydroxy-6-[bis(β-hydroxyethyl)amino]-3-nitrobenzene, 1-β-hydroxyethylamino-2-nitrobenzene, 1-hydroxy-4-β-hydroxyethylamino-3-nitrobenzene.

Among the azo direct dyes, there may be mentioned the cationic azo dyes described in patent applications WO 95/15144, WO 95/01772, EP 0,714,954, FR 2,822,696, FR 2,825,702, FR 2,825,625, FR 2,822,698, FR 2,822,693, FR 2,822,694, FR 2,829,926, FR 2,807,650, WO 02/078660, WO 02/100834, WO 02/100369 and FR 2,844,269 whose content forms an integral part of the invention.

Among these compounds, there may be mentioned most particularly 1,3-dimethyl-2-[[4-(dimethylamino)phenyl]-azo]-1H-imidazolium chloride, 1,3-dimethyl-2-[(4-aminophenyl)azo]-1H-imidazolium chloride, 1-methyl-4-[(methylphenylhydrazono)methyl]pyridinium methylsulphate.

The following dyes, which are described in COLOUR INDEX INTERNATIONAL 3$^{rd}$ edition, may also be mentioned among the azo direct dyes: Disperse Red 17, Acid Yellow 9, Acid Black 1, Basic Red 22, Basic Red 76, Basic Yellow 57, Basic Brown 16, Acid Yellow 36, Acid Orange 7, Acid Red 33, Acid Red 35, Basic Brown 17, Acid Yellow 23, Acid Orange 24, Disperse Black 9.

There may also be mentioned 1-(4'-aminodiphenylazo)-2-methyl-4-bis(β-hydroxyethyl)aminobenzene and 4-hydroxy-3-(2-methoxyphenylazo)-1-naphthalenesulphonic acid.

The following dyes may be mentioned among the quinone direct dyes: Disperse Red 15, Solvent Violet 13, Acid Violet 43, Disperse Violet 1, Disperse Violet 4, Disperse Blue 1, Disperse Violet 8, Disperse Blue 3, Disperse Red 11, Acid Blue 62, Disperse Blue 7, Basic Blue 22, Disperse Violet 15, Basic Blue 99, and the following compounds: 1-N-methyl-morpholiniumpropylamino-4-hydroxyanthraquinone, 1-aminopropylamino-4-methyl-aminoanthraquinone, 1-aminopropylaminoanthraquinone, 5-β-hydroxyethyl-1,4-diaminoanthraquinone, 2-aminoethyl-aminoanthraquinone, 1,4-bis(β,γ-dihydroxypropyl-amino)anthraquinone.

The following compounds may be mentioned among the azine dyes: Basic Blue 17, Basic Red 2.

The following compounds may be mentioned among the triarylmethane dyes: Basic Green 1, Acid Blue 9, Basic Violet 3, Basic Violet 14, Basic Blue 7, Acid Violet 49, Basic Blue 26, Acid Blue 7.

The following compounds may be mentioned among the indoamine dyes: 2-β-hydroxyethylamino-5-[bis(β-4'-hydroxyethyl)amino]anilino-1,4-benzoquinone, 2-β-hydroxyethylamino-5-(2'-methoxy-4'-amino)anilino-1,4-benzoquinone, 3-N-(2'-chloro-4'-hydroxy)phenylacetyl-amino-6-methoxy-1,4-benzoquinone imine, 3-N-(3'-chloro-4'-methylamino)phenylureido-6-methyl-1,4-benzoquinone imine, 3-[4'-N-(ethyl,carbamylmethyl)amino]-phenylureido-6-methyl-1,4-benzoquinone imine.

Among the natural direct dyes which can be used according to the invention, there may be mentioned lawsone, juglone, alizarin, purpurin, carminic acid, kermesic acid, purpurogallin, protocatechaldehyde, indigo, isatin, curcumin, spinulosin, apigenidin. It is also possible to use extracts or decoctions containing these natural dyes and in particular poultices or extracts based on henna.

When the ready-to-use bleaching composition in accordance with the invention comprises one or more direct dyes, they are generally present in a quantity of between 0.001 and 20% by weight approximately of the total weight of the ready-to-use composition, and still more preferably between 0.005 and 10% by weight approximately.

The oxidation dye precursors may be chosen from the oxidation bases and couplers conventionally used in the dyeing field.

By way of examples of oxidation bases, there may be mentioned para-phenylenediamines, double bases, para-aminophenols, ortho-aminophenols, heterocyclic bases and addition salts thereof.

Among the para-phenylenediamines, there may be mentioned, by way of example, para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylene-diamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylene-diamine, 2-β-acetylaminoethyloxy-para-phenylenediamine, N-(β-methoxyethyl)-para-phenylenediamine, 4-aminophenylpyrrolidine, 2-thienyl-para-phenylene-diamine, 2-β-hydroxyethylamino-5-aminotoluene, 3-hydroxy-1-(4'-aminophenyl)pyrrolidine and their addition salts with an acid.

Among the para-phenylenediamines mentioned above, there are particularly preferred para-phenylenediamine, para-tolylenediamine, 2-isopropyl-para-phenylenediamine, 2-β-hydroxyethyl-para-phenylenediamine, 2-β-hydroxy-ethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, and their addition salts with an acid.

Among the double bases, there may be mentioned, by way of examples, bisphenylalkylenediamines and bis-para-aminophenols.

Among the bisphenylalkylenediamines, there may be mentioned, by way of example, N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylene-diamine, N,N'-bis(4-aminophenyl)tetramethylenediamine, N,N'-bis(β-hydroxyethyl)-N,N'-bis(4-aminophenyl)tetra-methylene-diamine, N,N'-bis(4-methylaminophenyl)tetra-methylenediamine, N,N'-bis(ethyl)-N,N'-bis(4'-amino-3'-methylphenyl)ethylenediamine, 1,8-bis(2,5-diamino-phenoxy)-3,6-dioxaoctane, and their addition salts with an acid.

Among the para-aminophenols, there may be mentioned, by way of example, para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethyl-aminomethyl)phenol, 4-amino-2-fluorophenol, and their addition salts with an acid.

Among the ortho-aminophenols, there may be mentioned, by way of example, 2-aminophenol, 2-amino-5-methylphenol, 2-amino-6-methylphenol, 5-acetamido-2-aminophenol, and their addition salts with an acid.

Among the heterocyclic bases, there may be mentioned, by way of example, pyridine derivatives, pyrimidine derivatives and pyrazole derivatives.

Among the pyridine derivatives, there may be mentioned the compounds described for example in Patents GB 1,026,978 and GB 1,153,196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine, and their addition salts with an acid.

Other pyridine oxidation bases useful in the present invention are the oxidation bases 3-aminopyrazolo[1,5-a]pyridines or their addition salts which are described, for example, in Patent Application FR 2801308. By way of example, there may be mentioned pyrazolo[1,5-a]pyridin-3-ylamine; 2-acetylamino-pyrazolo[1,5-a]pyridin-3-ylamine; 2-morpholin-4-ylpyrazolo[1,5-a]pyridin-3-ylamine; 3-aminopyrazolo[1,5-a]pyridine-2-carboxylic acid; 2-methoxypyrazolo[1,5-a]pyridin-3-ylamino; (3-aminopyrazolo[1,5-a]pyridin-7-yl)methanol; 2-(3-aminopyrazolo[1,5-a]pyridin-5-yl)ethanol; 2-(3-aminopyrazolo[1,5-a]pyridin-7-yl)ethanol; (3-aminopyrazolo[1,5-a]pyridin-2-yl)methanol; 3,6-diaminopyrazolo[1,5-a]pyridine; 3,4-diaminopyrazolo[1,5-a]pyridine; pyrazolo[1,5-a]pyridine-3,7-diamine; 7-morpholin-4-ylpyrazolo[1,5-a]pyridin-3-ylamine; pyrazolo[1,5-a]pyridine-3,5-diamine; 5-morpholin-4-ylpyrazolo[1,5-a]pyridin-3-ylamine; 2-[(3-aminopyrazolo[1,5-a]pyridin-5-yl)-(2-hydroxyethyl)amino]ethanol; 2-[(3-aminopyrazolo[1,5-a]pyridin-7-yl)(2-hydroxyethyl)amino]ethanol; 3-aminopyrazolo[1,5-a]pyridin-5-ol; 3-aminopyrazolo[1,5-a]pyridin-4-ol, 3-aminopyrazolo[1,5-a]pyridin-6-ol; 3-aminopyrazolo[1,5-a]pyridin-7-ol; and their addition salts with an acid or with a base.

Among the pyrimidine derivatives, there may be mentioned the compounds described for example in Patents DE 2,359,399; JP 88-169,571; JP 05-63124; EP 0770375 or Patent Application WO 96/15765, such as 2,4,5,6-tetraaminopyrimidine, 4-hydroxy-2,5,6-triamino-pyrimidine, 2-hydroxy-4,5,6-triaminopyrimidine, 2,4-dihydroxy-5,6-diaminopyrimidine, 2,5,6-triamino-pyrimidine, and the pyrazolopyrimidine derivatives such as those mentioned in Patent Application FR-A-2,750,048 and among which there may be mentioned pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxy-ethyl)amino]ethanol, 2-[(7-aminopyrazolo[1,5-a]-pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine, 3-amino-5-methyl-7-imidazolylpropylamino-pyrazolo[1,5-a]pyrimidine and their addition salts with an acid and their tautomeric forms, when a tautomeric equilibrium exists.

Among the pyrazole derivatives, there may be mentioned the compounds described in Patents DE 3,843,892, DE 4,133,957 and Patent Applications WO 94/08969, WO 94/08970, FR-A-2,733,749 and DE 195 43 988 such as 4,5-diamino-1-methylpyrazole, 4,5-diamino-1-(β-hydroxy-ethyl)pyrazole, 3,4-diaminopyrazole, 4,5-diamino-1-(4'-chlorobenzyl)pyrazole, 4,5-diamino-1,3-dimethyl-pyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methyl-pyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and their addition salts with an acid.

When the ready-to-use bleaching composition in accordance with the invention comprises one or more oxidation bases, they are generally present in a quantity of between 0.001 and 10% by weight approximately of the total weight of the ready-to-use composition, preferably between 0.005 and 6% by weight approximately.

By way of examples of couplers, there may be mentioned meta-phenylenediamines, meta-aminophenols, meta-diphenols, naphthalene couplers, heterocyclic couplers and addition salts thereof.

By way of examples, there may be mentioned 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethyl-amino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxy-ethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene and their addition salts with an acid.

When the ready-to-use bleaching composition in accordance with the invention comprises one or more couplers, they are generally present in a quantity of between 0.001 and 10% by weight approximately of the total weight of the ready-to-use composition, preferably between 0.005 and 6% by weight approximately.

In general, the addition salts of the oxidation bases and couplers which can be used in the context of the invention are in particular chosen from the addition salts with an acid such as the hydrochlorides, hydrobromides, sulphates, citrates, succinates, tartrates, lactates, tosylates, benzenesulphonates, phosphates and acetates and the addition salts with a base such as sodium hydroxide, potassium hydroxide, ammonium hydroxide, amines or alkanolamines.

According to a particular embodiment, the ready-to-use bleaching composition in accordance with the invention comprises at least one alkaline agent as defined above. It may then result from mixing the direct emulsion in accordance with the invention with an aqueous composition comprising the alkaline agent(s) in an appropriate cosmetic medium.

According to another particular embodiment, the ready-to-use bleaching composition in accordance with the invention comprises at least one alkaline agent and at least one persalt as defined above. It may then result from mixing the direct emulsion in accordance with the invention with an anhydrous composition comprising the alkaline agent(s) and the persalt(s) in an appropriate cosmetic medium. It may also result from mixing the direct emulsion in accordance with the invention with an aqueous composition comprising the alkaline agent(s) in an appropriate cosmetic medium and an anhydrous composition comprising the persalt(s) in an appropriate cosmetic medium.

According to another particular embodiment, the ready-to-use bleaching composition in accordance with the invention comprises at least one direct dye as defined above. It may then result from mixing the direct emulsion in accordance with the invention with an aqueous composition comprising the direct dye(s) in an appropriate cosmetic medium.

According to another particular embodiment, the ready-to-use bleaching composition in accordance with the invention comprises at least one alkaline agent and at least one direct dye and/or at least one oxidation dye precursor as defined above. It may then result from mixing the direct emulsion in accordance with the invention with an aqueous composition comprising, in an appropriate cosmetic medium, the alkaline agent(s) and the direct dye(s) and/or the oxidation dye precursor(s). It may also result from mixing the direct emulsion in accordance with the invention with an aqueous composition comprising the alkaline agent(s) in an appropriate cosmetic medium and an aqueous composition comprising the direct dye(s) and/or the oxidation dye precursor(s) in an appropriate cosmetic medium.

According to another particular embodiment, the ready-to-use bleaching composition in accordance with the invention comprises at least one alkaline agent, at least one persalt and at least one direct dye as defined above. It may then result from mixing the direct emulsion in accordance with the invention with an anhydrous composition comprising the alkaline agent(s) and the persalt(s) in an appropriate cosmetic medium and an aqueous composition comprising the direct dye(s) in an appropriate cosmetic medium. It may also result from mixing the direct emulsion in accordance with the invention with an aqueous composition comprising the alkaline agent(s) in an appropriate cosmetic medium, an anhydrous composition comprising the persalt(s) in an appropriate cosmetic medium and an aqueous composition comprising the direct dye(s) in an appropriate cosmetic medium.

The compositions comprising the persalt(s) are anhydrous. They may also comprise customary additives in the field, in particular water-soluble thickening polymers, fillers such as clays or amorphous silica, binders such as vinylpyrrolidone, lubricants such as polyol stearates or alkali or alkaline-earth metal stearates, and agents for controlling the emission of oxygen such as magnesium carbonate or oxide, dyeing agents or mattifying agents such as titanium oxides or anionic, nonionic, cationic or amphoteric surfactants, vitamins.

By way of illustration, the content of additive(s) represents from 0.01 to 40% by weight, preferably from 0.1 to 30% by weight relative to the total weight of the compositions.

The anhydrous compositions may be provided in powdered or paste form. In the case where they are provided in paste form, they further comprise an organic inert liquid chosen from polydecenes of formula $C_{10n}H_{[(20n)+2]}$ in which n varies from 3 to 9 and preferably from 3 to 7, fatty alcohol or fatty acid esters, $C_{12}$-$C_{24}$ fatty acid esters or diesters of sugars, cyclic ethers or cyclic esters, silicone oils, mineral oils or vegetable oils.

The other compositions are preferably aqueous. The appropriate cosmetic medium for these compositions generally contains water or a mixture of water and at least one organic solvent for solubilizing the compounds which might not be sufficiently soluble in water. By way of organic solvent, there may for example be mentioned $C_1$-$C_4$ lower alkanols such as ethanol and isopropanol; glycerol; glycols and glycol ethers such as 2-butoxyethanol, propylene glycol, propylene glycol monomethyl ether, and aromatic alcohols such as benzyl alcohol or phenoxyethanol, analogous products and mixtures thereof.

The solvents may be present in proportions preferably between 1 and 40% by weight relative to the total weight of the composition, and more preferably still between 5 and 30% by weight approximately.

These compositions may also contain various adjuvants conventionally used in compositions for bleaching hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, and in particular the associative thickeners, anionic, cationic, nonionic and amphoteric polymers, antioxidants, penetrating agents, sequestrants, perfumes, buffers, dispersing agents, conditioning agents such as, for example, modified or unmodified, volatile or nonvolatile silicones, film-forming agents, ceramides, preservatives, opacifying agents.

The above adjuvants are generally present in a quantity, for each of them, of between 0.01 and 20% by weight relative to the weight of the composition.

Of course, persons skilled in the art will be careful to choose this or these optional additional compounds such that the advantageous properties intrinsically attached to these compositions are not, or not substantially, impaired by the addition(s) envisaged.

These compositions may be provided in various forms, such as in the form of liquids, creams, gels, or in any other appropriate cosmetic form.

The pH of the ready-to-use bleaching composition in accordance with the invention is preferably between 4 and 11. It is preferably alkaline, and more preferably still between 7 and 11.

The bleaching method in accordance with the present invention consists in applying to the keratin fibers a direct emulsion or a ready-to-use bleaching composition in accordance with the invention as defined above.

The subject of the present invention is also a kit for bleaching keratin fibers, containing a direct emulsion in accordance with the invention and one or more compositions in which at least one alkaline agent and/or at least one persalt and/or at least one dye precursor and/or at least one direct dye as defined above are distributed.

According to a particular embodiment of the invention, the kit in accordance with the invention contains a direct emulsion in accordance with the invention and an aqueous composition comprising at least one alkaline agent as defined above, preferably in an appropriate cosmetic medium.

According to another particular embodiment of the invention, the kit in accordance with the invention contains a direct emulsion in accordance with the invention, an anhydrous composition comprising at least one persalt as defined above preferably in an appropriate cosmetic medium and an aqueous composition comprising at least one alkaline agent as defined above preferably in an appropriate cosmetic medium.

According to another particular embodiment of the invention, the kit in accordance with the invention contains a direct emulsion in accordance with the invention and an anhydrous composition comprising at least one alkaline agent and at least one persalt as defined above preferably in an appropriate cosmetic medium.

According to another particular embodiment of the invention, the kit in accordance with the invention contains a direct emulsion in accordance with the invention and an aqueous composition comprising at least one direct dye as defined above preferably in an appropriate cosmetic medium.

According to another particular embodiment of the invention, the kit in accordance with the invention contains a direct emulsion in accordance with the invention, an aqueous composition comprising at least one alkaline agent as defined above in an appropriate cosmetic medium and an aqueous composition comprising at least one direct dye and/or at least one oxidation dye precursor as defined above preferably in an appropriate cosmetic medium.

According to another particular embodiment of the invention, the kit in accordance with the invention contains a direct emulsion in accordance with the invention and an aqueous composition comprising, in an appropriate cosmetic medium, at least one alkaline agent and at least one direct dye and/or at least one oxidation dye precursor as defined above.

According to another particular embodiment of the invention, the kit in accordance with the invention contains a direct emulsion in accordance with the invention, an anhydrous composition comprising at least one alkaline agent and at least one persalt as defined above in an appropriate cosmetic medium and an aqueous composition comprising at least one direct dye as defined above preferably in an appropriate cosmetic medium.

According to another particular embodiment of the invention, the kit in accordance with the invention contains a direct emulsion in accordance with the invention, an anhydrous composition comprising at least one persalt as defined above in an appropriate cosmetic medium, an aqueous composition comprising at least one alkaline agent as defined above in an appropriate cosmetic medium and an aqueous composition comprising at least one direct dye as defined above preferably in an appropriate cosmetic medium.

The subject of the present invention is also the use, for bleaching keratin fibers, of a direct emulsion or of a ready-to-use bleaching composition in accordance with the invention as defined above.

The following examples serve to illustrate the invention without however being limiting in nature.

EXAMPLE

The following oxidizing composition 1 was prepared:

| OXIDIZING COMPOSITION 1 | |
|---|---|
| Paraffin oil | 50 g |
| Lauryl sulphate | 2 g |
| Oxyethylenated stearyl alcohol (100 EO) or Steareth-100 | 1 g |
| Polyacrylic acid Carbopol 940 marketed by the company Noveon | 2 g |
| Hydrogen peroxide | 6 g |
| Sodium stannate · 6H$_2$O | 0.04 g |
| Diethylenetriaminepentaacetic acid | 0.015 g |
| Demineralized water | qs 100 g |

The oxidizing composition 1 was mixed at the time of use with a bleaching powder containing 50% of persulphates, 24.1% of silicates and 2.6% of chloride of ammonium, with a bleaching powder/oxidizing composition ratio equal to 1/1.5.

The mixture obtained was applied to 2.5 g of locks of natural chestnut brown hair in an amount of 10 g of mixture per 1 g of hair. After a leave-in time of 35 minutes, the locks were rinsed, washed with a standard shampoo, rinsed again and then dried.

The glints obtained were an intense coppery dark blond. The above written description of the invention provides a manner and process of making and using it such that any person skilled in this art is enabled to make and use the same, this enablement being provided in particular for the subject matter of the appended claims, which make up a part of the original description and including a direct emulsion for bleaching keratin fibers, comprising an inert phase containing a nonoxygenated and nonperfluorinated liquid compound having a water-solubility at 25° C. of less than 1% and an aqueous hydrogen peroxide solution, the inert phase representing at least 20% by weight of the total weight of the direct emulsion.

As used herein, the phrases "selected from the group consisting of," "chosen from," and the like include mixtures of the specified materials. Terms such as "contain(s)" and the like as used herein are open terms meaning 'including at least' unless otherwise specifically noted.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

The invention claimed is:

1. A direct emulsion, comprising an inert phase and an aqueous hydrogen peroxide solution, said inert phase comprising at least one nonoxygenated and nonperfluorinated liquid compound having a water-solubility at 25° C. of less than 1%, the inert phase representing at least 20% by weight of the total weight of the direct emulsion.

2. The direct emulsion according to claim 1, in which the inert phase comprises at least one of polyalphaolefins, polybutenes and polyisobutenes, mineral oils, paraffin oils, polystyrene and polyisoprene block copolymers, and mixtures thereof.

3. The direct emulsion according to claim 1, in which the inert phase represents between 20 and 95% by weight of the total weight of the direct emulsion.

4. The direct emulsion according to claim 1, in which the inert phase represents between 30 and 90% by weight of the total weight of the direct emulsion.

5. The direct emulsion according to claim 1, in which the hydrogen peroxide concentration is between 1 and 20% by weight of the total weight of the direct emulsion.

6. The direct emulsion according to claim 1, in which the hydrogen peroxide concentration is between 2 and 12% by weight of the total weight of the direct emulsion.

7. The direct emulsion according to claim 1, further comprising at least one compound chosen from surfactants, amphiphilic polymers and thickening polymers.

8. The direct emulsion according to claim 1, further comprising at least one surfactant chosen from anionic, nonionic, cationic and amphoteric surfactants having one or more linear or branched $C_6$-$C_{22}$ alkylated chains and/or one or more perfluorinated chains.

9. The direct emulsion according to claim 1, further comprising at least one water-soluble or water-dispersible amphiphilic block copolymer, oxyethylenated or nonoxyethylenated, telechelic or graft associative polymer bearing on their main chain $C_6$-$C_{22}$ alkyl and/or aryl groups, it being possible for these polymers to have a cationic, anionic, amphoteric or nonionic charge.

10. The direct emulsion according to claim 1, further comprising at least one thickening polymer chosen from crosslinked acrylic polymers, natural or modified polysaccharides.

11. The direct emulsion according to claim 7, in which the compound(s) chosen from surfactants, amphiphilic polymers and thickening polymers are each present in a quantity of between 0.1 and 30% by weight of the total weight of the direct emulsion.

12. The direct emulsion according to claim 1, whose pH is less than 5.

13. A ready-to-use bleaching composition resulting from mixing a direct emulsion as defined in claim 1 with one or more compositions comprising at least one alkaline agent and/or at least one persalt and/or at least one direct dye and/or at least one oxidation dye precursor.

14. The ready-to-use bleaching composition according to claim 13, resulting from mixing the direct emulsion with one or more alkaline agent(s) chosen from organic amines, ammonium hydroxide and silicates.

15. The ready-to-use bleaching composition according to claim 14, in which the alkaline agent(s) are present in a quantity of between 0.01 and 40% by weight of the total weight of the ready-to-use composition.

16. The ready-to-use bleaching composition according to claim 13, resulting from mixing the direct emulsion with at least one persalt chosen from ammonium and alkali metal perborates, percarbonates and persulphates.

17. The ready-to-use bleaching composition according to claim 16, in which the persalt(s) are present in a quantity of between 10 and 70% by weight of the total weight of the ready-to-use composition.

18. The ready-to-use bleaching composition according to claim 13, resulting from mixing the direct emulsion a with at least one direct dye, wherein said direct dye is present in a quantity of between 0.001 and 20% by weight of the total weight of the ready-to-use composition.

19. The ready-to-use bleaching composition according to claim 13, resulting from mixing the direct emulsion a with at least one dye precursor, and in which the dye precursor(s) are chosen from oxidation bases and couplers.

20. The ready-to-use bleaching composition according to claim 19, in which the dye precursor(s) are present in a quantity of between 0.001 and 10% by weight of the total weight of the ready-to-use composition.

21. A method for bleaching keratin fibers, comprising contacting said fibers with the direct emulsion as defined in claim 1.

22. A kit for bleaching keratin fibers, comprising:
a direct emulsion as defined in claim 1, and
at least one composition comprising at least one of an alkaline agent, a persalt, a dye precursor, and a direct dye.

* * * * *